(12) United States Patent
VanCamp et al.

(10) Patent No.: US 12,691,275 B2
(45) Date of Patent: Jul. 28, 2026

(54) PERCUTANEOUS CIRCULATORY SUPPORT SYSTEM FACILITATING REDUCED HEMOLYSIS

(71) Applicant: Boston Scientific Scimed Inc., Maple Grove, MN (US)

(72) Inventors: Daniel H. VanCamp, Elk River, MN (US); Steven R. Larsen, Lino Lakes, MN (US); Jeffrey Lucas, Hopkins, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 627 days.

(21) Appl. No.: 17/988,112

(22) Filed: Nov. 16, 2022

(65) Prior Publication Data

US 2023/0149691 A1 May 18, 2023

Related U.S. Application Data

(60) Provisional application No. 63/279,925, filed on Nov. 16, 2021.

(51) Int. Cl.
| | |
|---|---|
| *A61M 60/126* | (2021.01) |
| *A61M 60/216* | (2021.01) |
| *A61M 60/408* | (2021.01) |
| *A61M 60/818* | (2021.01) |

(52) U.S. Cl.
CPC ........ *A61M 60/126* (2021.01); *A61M 60/216* (2021.01); *A61M 60/408* (2021.01); *A61M 60/818* (2021.01)

(58) Field of Classification Search
None
See application file for complete search history.

(56) References Cited

U.S. PATENT DOCUMENTS

| | | | |
|---|---|---|---|
| 5,021,048 A | 6/1991 | Buckholtz | |
| 5,145,333 A | 9/1992 | Smith | |
| 5,211,546 A * | 5/1993 | Isaacson | A61M 60/806 |
| | | | 604/151 |
| 5,507,629 A | 4/1996 | Jarvik | |
| 5,527,159 A | 6/1996 | Bozeman, Jr. et al. | |
| 5,611,679 A | 3/1997 | Ghosh et al. | |
| 5,692,882 A | 12/1997 | Bozeman, Jr. et al. | |

(Continued)

FOREIGN PATENT DOCUMENTS

| | | |
|---|---|---|
| DE | 3338002 A1 | 5/1985 |
| EP | 0847767 B1 | 2/2005 |

(Continued)

OTHER PUBLICATIONS

US 9,067,007 B2, 06/2015, Tanner et al. (withdrawn)

(Continued)

*Primary Examiner* — Mallika D Fairchild
(74) *Attorney, Agent, or Firm* — Seager, Tufte & Wickhem LLP

(57) ABSTRACT

A percutaneous circulatory support device includes an impeller housing having an inlet and an outlet. A shaft is rotatably fixed relative to the impeller housing. An impeller is configured to rotate relative to the shaft and the impeller housing to cause blood to flow into the inlet, through the impeller housing, and out of the outlet.

18 Claims, 8 Drawing Sheets

(56)                References Cited

U.S. PATENT DOCUMENTS

| | | | |
|---|---|---|---|
| 5,911,685 A * | 6/1999 | Siess | A61M 60/178 600/16 |
| 5,928,131 A | 7/1999 | Prem | |
| 5,947,703 A | 9/1999 | Nojiri et al. | |
| 5,947,892 A | 9/1999 | Benkowski et al. | |
| 5,964,694 A | 10/1999 | Siess et al. | |
| 6,056,520 A | 5/2000 | Nguyen et al. | |
| 6,135,729 A | 10/2000 | Aber | |
| 6,139,487 A | 10/2000 | Siess | |
| 6,176,822 B1 | 1/2001 | Nix et al. | |
| 6,176,848 B1 * | 1/2001 | Rau | F04D 29/0467 600/16 |
| 6,201,329 B1 | 3/2001 | Chen | |
| 6,227,820 B1 | 5/2001 | Jarvik | |
| 6,264,635 B1 | 7/2001 | Wampler et al. | |
| 6,447,266 B2 | 9/2002 | Antaki et al. | |
| 7,841,976 B2 | 11/2010 | McBride et al. | |
| 7,927,068 B2 | 4/2011 | McBride et al. | |
| 7,972,122 B2 | 7/2011 | Larose et al. | |
| 8,007,254 B2 | 8/2011 | Larose et al. | |
| 8,043,074 B2 | 10/2011 | Tada | |
| 8,376,707 B2 | 2/2013 | McBride et al. | |
| 8,512,012 B2 | 8/2013 | Akdis et al. | |
| 8,591,393 B2 | 11/2013 | Walters et al. | |
| 8,597,170 B2 | 12/2013 | Walters et al. | |
| 8,684,904 B2 | 4/2014 | Campbell et al. | |
| 8,721,517 B2 | 5/2014 | Zeng et al. | |
| 8,770,945 B2 | 7/2014 | Ozaki et al. | |
| 8,827,661 B2 | 9/2014 | Mori | |
| 8,992,163 B2 | 3/2015 | McBride et al. | |
| 9,067,005 B2 | 6/2015 | Ozaki et al. | |
| 9,072,825 B2 | 7/2015 | Pfeffer et al. | |
| 9,091,271 B2 | 7/2015 | Bourque | |
| 9,138,518 B2 | 9/2015 | Yuen et al. | |
| 9,162,017 B2 | 10/2015 | Evans et al. | |
| 9,199,020 B2 | 12/2015 | Siess | |
| 9,308,302 B2 | 4/2016 | Zeng | |
| 9,308,304 B2 | 4/2016 | Peters et al. | |
| 9,314,557 B2 | 4/2016 | Ricci et al. | |
| 9,327,067 B2 | 5/2016 | Zeng et al. | |
| 9,364,592 B2 | 6/2016 | McBride et al. | |
| 9,364,593 B2 | 6/2016 | McBride et al. | |
| 9,364,594 B2 | 6/2016 | Nüsser et al. | |
| 9,381,288 B2 | 7/2016 | Schenck et al. | |
| 9,398,743 B1 | 7/2016 | Fox et al. | |
| 9,421,311 B2 | 8/2016 | Tanner et al. | |
| 9,446,179 B2 | 9/2016 | Keenan et al. | |
| 9,616,157 B2 | 4/2017 | Akdis | |
| 9,675,740 B2 | 6/2017 | Zeng et al. | |
| 9,717,833 B2 | 8/2017 | McBride et al. | |
| 9,737,652 B2 | 8/2017 | Larose et al. | |
| 9,770,543 B2 | 9/2017 | Tanner et al. | |
| 9,872,947 B2 | 1/2018 | Keenan et al. | |
| 9,895,476 B2 | 2/2018 | Larose et al. | |
| 9,907,890 B2 | 3/2018 | Muller | |
| 9,956,332 B2 | 5/2018 | Larose et al. | |
| 9,962,475 B2 | 5/2018 | Yuen et al. | |
| 9,964,115 B2 | 5/2018 | Scheckel | |
| 10,029,037 B2 | 7/2018 | Muller et al. | |
| 10,039,872 B2 | 8/2018 | Zeng et al. | |
| 10,071,192 B2 | 9/2018 | Zeng | |
| 10,086,121 B2 | 10/2018 | Fitzgerald et al. | |
| 10,105,475 B2 | 10/2018 | Muller | |
| 10,117,980 B2 | 11/2018 | Keenan et al. | |
| 10,149,932 B2 | 12/2018 | McBride et al. | |
| 10,215,187 B2 | 2/2019 | McBride et al. | |
| 10,232,099 B2 | 3/2019 | Peters et al. | |
| 10,251,985 B2 | 4/2019 | Larose et al. | |
| 10,251,986 B2 | 4/2019 | Larose et al. | |
| 10,478,539 B2 | 11/2019 | Pfeffer et al. | |
| 10,478,540 B2 | 11/2019 | Scheckel et al. | |
| 10,525,178 B2 | 1/2020 | Zeng | |
| 10,576,192 B2 | 3/2020 | Muller et al. | |
| 10,576,193 B2 | 3/2020 | Tanner et al. | |
| 10,704,553 B2 | 7/2020 | Janeczek et al. | |

| | | | |
|---|---|---|---|
| 10,709,829 B2 | 7/2020 | Muller | |
| 10,709,830 B2 | 7/2020 | Tanner et al. | |
| 10,765,789 B2 | 9/2020 | Zeng et al. | |
| 10,780,208 B2 | 9/2020 | Siess et al. | |
| 10,786,610 B2 | 9/2020 | Zeng | |
| 10,799,624 B2 | 10/2020 | Pfeffer et al. | |
| 10,842,921 B2 | 11/2020 | Siess et al. | |
| 10,864,308 B2 | 12/2020 | Muller et al. | |
| 10,864,309 B2 | 12/2020 | McBride et al. | |
| 10,874,783 B2 | 12/2020 | Pfeffer et al. | |
| 10,894,115 B2 | 1/2021 | Pfeffer et al. | |
| 10,918,774 B2 | 2/2021 | Stanfield et al. | |
| 10,960,116 B2 | 3/2021 | Yuen et al. | |
| 10,973,967 B2 | 4/2021 | Nyikos et al. | |
| 10,980,927 B2 | 4/2021 | Pfeffer et al. | |
| 11,058,865 B2 | 7/2021 | Fitzgerald et al. | |
| 11,097,092 B2 | 8/2021 | Siess et al. | |
| 11,107,626 B2 | 8/2021 | Siess et al. | |
| 11,123,539 B2 | 9/2021 | Pfeffer et al. | |
| 11,129,978 B2 | 9/2021 | Pfeffer et al. | |
| 11,167,124 B2 | 11/2021 | Pfeffer et al. | |
| 11,219,755 B2 | 1/2022 | Siess et al. | |
| 11,229,786 B2 | 1/2022 | Zeng et al. | |
| 11,235,138 B2 | 2/2022 | Gross-Hardt et al. | |
| 11,253,693 B2 | 2/2022 | Pfeffer et al. | |
| 11,260,213 B2 | 3/2022 | Zeng et al. | |
| 11,273,301 B2 | 3/2022 | Pfeffer et al. | |
| 11,311,712 B2 | 4/2022 | Zeng et al. | |
| 11,338,124 B2 | 5/2022 | Pfeffer et al. | |
| 11,357,967 B2 | 6/2022 | Zeng et al. | |
| 11,400,276 B2 | 8/2022 | Chopra et al. | |
| 11,471,664 B2 | 10/2022 | Xu et al. | |
| 11,497,896 B2 | 11/2022 | Tanner et al. | |
| 11,517,736 B2 | 12/2022 | Earles et al. | |
| 11,569,015 B2 | 1/2023 | Mourran et al. | |
| 11,583,659 B2 | 2/2023 | Pfeffer et al. | |
| 11,628,294 B2 | 4/2023 | Chopra et al. | |
| 11,648,388 B2 | 5/2023 | Siess et al. | |
| 11,672,968 B2 | 6/2023 | Antaki | |
| 11,708,833 B2 | 7/2023 | McBride et al. | |
| 11,754,075 B2 | 9/2023 | Schuelke et al. | |
| 11,786,700 B2 | 10/2023 | Pfeffer et al. | |
| 11,813,443 B2 | 11/2023 | Hanson et al. | |
| 2003/0233021 A1 | 12/2003 | Nose et al. | |
| 2006/0222533 A1 | 10/2006 | Reeves et al. | |
| 2008/0114339 A1 | 5/2008 | McBride et al. | |
| 2009/0060743 A1 | 3/2009 | McBride et al. | |
| 2009/0093764 A1 | 4/2009 | Pfeffer et al. | |
| 2009/0171137 A1 | 7/2009 | Farnan et al. | |
| 2011/0004046 A1 * | 1/2011 | Campbell | A61M 60/422 600/16 |
| 2011/0237863 A1 | 9/2011 | Ricci et al. | |
| 2011/0238172 A1 | 9/2011 | Akdis | |
| 2013/0338559 A1 | 12/2013 | Franano et al. | |
| 2014/0010686 A1 | 1/2014 | Tanner et al. | |
| 2014/0336446 A1 | 11/2014 | Rodefeld | |
| 2016/0271308 A1 | 9/2016 | Larose et al. | |
| 2017/0043074 A1 | 2/2017 | Siess | |
| 2017/0296725 A1 | 10/2017 | Peters et al. | |
| 2018/0303990 A1 | 10/2018 | Siess et al. | |
| 2018/0311423 A1 | 11/2018 | Zeng et al. | |
| 2019/0275224 A1 | 9/2019 | Hanson et al. | |
| 2020/0121835 A1 * | 4/2020 | Farago | A61M 60/216 |
| 2020/0306434 A1 * | 10/2020 | VanCamp | A61M 60/825 |
| 2021/0015982 A1 | 1/2021 | Kerkhoffs et al. | |
| 2021/0023282 A1 | 1/2021 | Siess et al. | |
| 2021/0038785 A1 | 2/2021 | Siess et al. | |
| 2021/0069393 A1 | 3/2021 | Schauer et al. | |
| 2021/0106810 A1 | 4/2021 | Pfeffer et al. | |
| 2022/0134082 A1 | 5/2022 | Pfeffer et al. | |
| 2022/0384070 A1 | 12/2022 | Mourran | |
| 2023/0040593 A1 | 2/2023 | Liu et al. | |

FOREIGN PATENT DOCUMENTS

| | | | |
|---|---|---|---|
| EP | 2301598 B1 | 7/2017 | |
| EP | 3352808 B1 | 9/2023 | |

(56)  References Cited

FOREIGN PATENT DOCUMENTS

| JP | 2011503410 A | 1/2011 |
| WO | 9500185 A1 | 1/1995 |
| WO | 0117581 A2 | 3/2001 |

OTHER PUBLICATIONS

International Search Report and Written Opinion for International Application No. PCT/US2022/050053, dated Mar. 6, 2023. (110 pages).
International Search Report and Written Opinion dated Mar. 6, 2023 for International Application No. PCT/US2022/050053.

* cited by examiner

200

PERCUTANEOUS CIRCULATORY SUPPORT SYSTEM FACILITATING REDUCED HEMOLYSIS

CROSS-REFERENCE TO RELATED APPLICATION

The present application claims priority to Provisional Application No. 63/279,925, filed Nov. 16, 2021, which is herein incorporated by reference in its entirety.

TECHNICAL FIELD

The present disclosure relates to percutaneous circulatory support systems. More specifically, the disclosure relates to percutaneous circulatory support devices that facilitate reduced hemolysis.

BACKGROUND

Percutaneous circulatory support devices such as blood pumps can provide transient support for up to approximately several weeks in patients with compromised heart function or cardiac output. Operation of such blood pumps, however, may cause some amount of hemodynamic shear, which in turn may result in hemolysis (that is, the rupture or destroying of blood cells). High rates of hemolysis can in turn cause acute kidney injury or other complications. Accordingly, there is a need for improved blood pumps that facilitate reduced hemolysis.

SUMMARY

In an Example 1, a percutaneous circulatory support device comprises an impeller housing comprising an inlet and an outlet; a shaft rotatably fixed relative to the impeller housing; and an impeller configured to rotate relative to the shaft and the impeller housing to cause blood to flow into the inlet, through the impeller housing, and out of the outlet.

In an Example 2, the percutaneous circulatory support device of Example 1, wherein the impeller is disposed within the impeller housing.

In an Example 3, the percutaneous circulatory support device of either of Example 1 or 2, wherein the impeller is rotatably supported by the shaft.

In an Example 4, the percutaneous circulatory support device of any of Examples 1-3, further comprising a motor being operable to rotatably drive the impeller relative to the shaft and the impeller housing and thereby cause blood to flow into the inlet, through the impeller housing, and out of the outlet.

In an Example 5, the percutaneous circulatory support device of any of Examples 1-4, further comprising a thrust bearing coupling the impeller to the impeller housing.

In an Example 6, the percutaneous circulatory support device of Example 5, wherein the thrust bearing is a proximal thrust bearing, and further comprising a distal thrust bearing coupling the impeller to the impeller housing.

In an Example 7, the percutaneous circulatory support device of any of Examples 1-6, further comprising an impeller assembly, the impeller assembly comprising the impeller and an inner tube rotatably supported by the shaft, and the impeller is rotatably fixed relative to the inner tube.

In an Example 8, the percutaneous circulatory support device of any of Examples 1-7, wherein the impeller housing comprises a proximal impeller housing portion and a distal impeller housing portion, the proximal impeller housing portion and the distal impeller housing portion being completely disposed apart and thereby forming the outlet therebetween.

In an Example 9, the percutaneous circulatory support device of Example 8, wherein the distal impeller housing portion comprises the inlet.

In an Example 10, the percutaneous circulatory support device of any of Examples 1-7, wherein the impeller housing comprises a proximal impeller housing portion and a distal impeller housing portion, the proximal impeller housing portion and the distal impeller housing portion only being indirectly coupled via the shaft, and the proximal impeller housing and the distal impeller housing thereby forming the outlet therebetween.

In an Example 11, the percutaneous circulatory support device of Example 10, wherein the distal impeller housing portion comprises the inlet.

In an Example 12, a percutaneous circulatory support device comprises a motor; an impeller housing comprising an inlet and an outlet; a distal support coupled to the impeller housing opposite the motor; a shaft rotatably fixed relative to the impeller housing and the distal support; and an impeller rotatably supported by the shaft; and wherein the motor is operable to rotatably drive the impeller relative to the impeller housing and thereby cause blood to flow into the inlet, through the impeller housing, and out of the outlet.

In an Example 13, the percutaneous circulatory support device of Example 12, further comprising a thrust bearing coupled to the impeller.

In an Example 14, the percutaneous circulatory support device of Example 13, wherein the thrust bearing is a proximal thrust bearing, and further comprising a distal thrust bearing coupled to the impeller.

In an Example 15, the percutaneous circulatory support device of any of Examples 12-14, further comprising an impeller assembly, the impeller assembly comprising the impeller and an inner tube rotatably supported by the shaft, and the impeller is rotatably fixed relative to the inner tube.

In an Example 16, a percutaneous circulatory support device comprises an impeller housing comprising an inlet and an outlet; a shaft rotatably fixed relative to the impeller housing; and an impeller disposed within the impeller housing and rotatably supported by the shaft, the impeller configured to rotate relative to the shaft and the impeller housing to cause blood to flow into the inlet, through the impeller housing, and out of the outlet.

In an Example 17, the percutaneous circulatory support device of Example 16, further comprising a motor being operable to rotatably drive the impeller relative to the shaft and the impeller housing and thereby cause blood to flow into the inlet, through the impeller housing, and out of the outlet.

In an Example 18, the percutaneous circulatory support device of Example 16, further comprising a thrust bearing coupling the impeller to the impeller housing.

In an Example 19, the percutaneous circulatory support device of Example 18, wherein the thrust bearing is a proximal thrust bearing, and further comprising a distal thrust bearing coupling the impeller to the impeller housing.

In an Example 20, the percutaneous circulatory support device of Example 16, further comprising an impeller assembly, the impeller assembly comprising the impeller and an inner tube rotatably supported by the shaft, and the impeller is rotatably fixed relative to the inner tube.

In an Example 21, the percutaneous circulatory support device of Example 20, further comprising: a motor; a drive magnet operably coupled to the motor; and a driven magnet operably coupled to the drive magnet, and the inner tube and the impeller being rotatably fixed relative to the driven magnet; wherein the motor is operable to rotatably drive the impeller, via the drive magnet and the driven magnet, and thereby cause blood to flow into the inlet, through the impeller housing, and out of the outlet.

In an Example 22, the percutaneous circulatory support device of Example 16, wherein the impeller housing comprises a proximal impeller housing portion and a distal impeller housing portion, the proximal impeller housing portion and the distal impeller housing portion being completely disposed apart and thereby forming the outlet therebetween.

In an Example 23, the percutaneous circulatory support device of Example 22, wherein the distal impeller housing portion comprises the inlet.

In an Example 24, the percutaneous circulatory support device of Example 16, wherein the impeller housing comprises a proximal impeller housing portion and a distal impeller housing portion, the proximal impeller housing portion and the distal impeller housing portion only being indirectly coupled via the shaft, and the proximal impeller housing and the distal impeller housing thereby forming the outlet therebetween.

In an Example 25, the percutaneous circulatory support device of Example 24, wherein the distal impeller housing portion comprises the inlet.

In an Example 26, a percutaneous circulatory support device comprises: a motor; an impeller housing comprising an inlet and an outlet; a distal support coupled to the impeller housing opposite the motor; a shaft rotatably fixed relative to the impeller housing and the distal support; and an impeller disposed within the impeller housing and rotatably supported by the shaft; and wherein the motor is operable to rotatably drive the impeller relative to the impeller housing and thereby cause blood to flow into the inlet, through the impeller housing, and out of the outlet.

In an Example 27, the percutaneous circulatory support device of Example 26, further comprising a thrust bearing coupled to the impeller.

In an Example 28, the percutaneous circulatory support device of Example 27, wherein the thrust bearing is a proximal thrust bearing, and further comprising a distal thrust bearing coupled to the impeller.

In an Example 29, the percutaneous circulatory support device of Example 26, further comprising an impeller assembly, the impeller assembly comprising the impeller and an inner tube rotatably supported by the shaft, and the impeller is rotatably fixed relative to the inner tube.

In an Example 30, the percutaneous circulatory support device of Example 29, further comprising: a drive magnet operably coupled to the motor; and a driven magnet operably coupled to the drive magnet, the inner tube and the impeller being rotatably fixed relative to the driven magnet; wherein the motor is operable to rotatably drive the impeller, via the drive magnet and the driven magnet, and thereby cause blood to flow into the inlet, through the impeller housing, and out of the outlet.

In an Example 31, a method of manufacturing a percutaneous circulatory support device comprises: coupling a shaft to an impeller housing such that the shaft is rotatably fixed relative to the impeller housing; coupling a shaft to an impeller housing such that the shaft is rotatably fixed relative to the impeller housing; coupling an impeller to the shaft such that the impeller is disposed within the impeller housing and rotatably supported by the shaft; and operatively coupling the impeller to a motor.

In an Example 32, the method of Example 31, further comprising coupling a thrust bearing to the shaft and the impeller housing before coupling the impeller to the shaft.

In an Example 33, the method of Example 31, further comprising coupling an inner tube to the impeller such that the impeller is rotatably fixed relative to the inner tube, and wherein coupling the impeller to the shaft comprises together coupling the inner tube and the impeller to the shaft.

In an Example 34, the method of Example 33, further comprising coupling a driven magnet to the inner tube such that the driven magnet is rotatably fixed relative to the inner tube, and wherein together coupling the inner tube and the impeller to the shaft comprises together coupling the inner tube, the driven magnet, and the impeller to the shaft.

In an Example 35, the method of Example 31, further comprising coupling a proximal thrust bearing and a distal thrust bearing to the impeller before coupling the impeller to the shaft.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
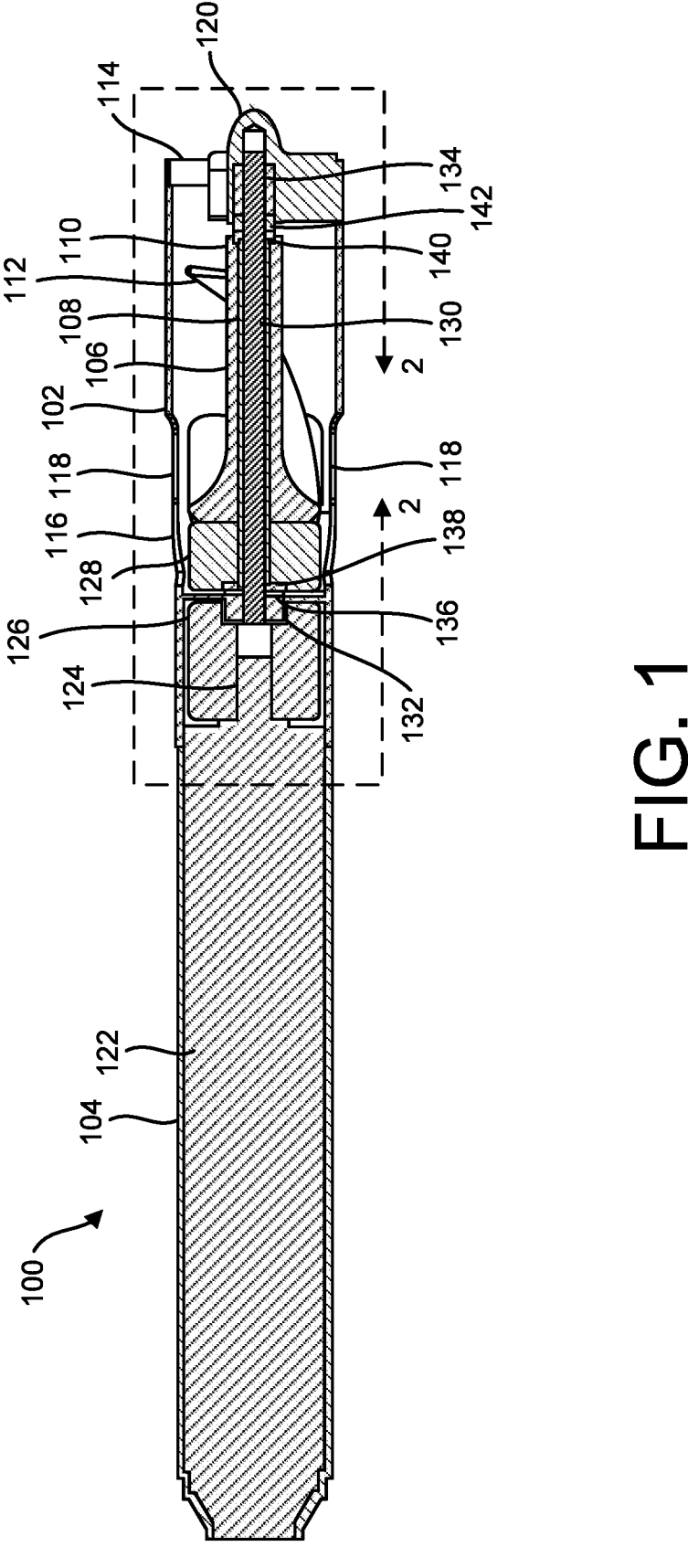
FIG. 1 is a side sectional view of an illustrative mechanical circulatory support device (also referred to herein, interchangeably, as a "blood pump"), in accordance with embodiments of the subject matter disclosed herein.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 depicts a side sectional view of an illustrative mechanical circulatory support device 100 (also referred to herein, interchangeably, as a "blood pump") in accordance with embodiments of the subject matter disclosed herein. The blood pump 100 may form part of a percutaneous circulatory support system, together with a guidewire and an introducer sheath (not shown). More specifically, the guidewire and the introducer sheath may facilitate percutaneously delivering the blood pump 100 to a target location within a patient, such as within the patient's heart.

Figure 2:
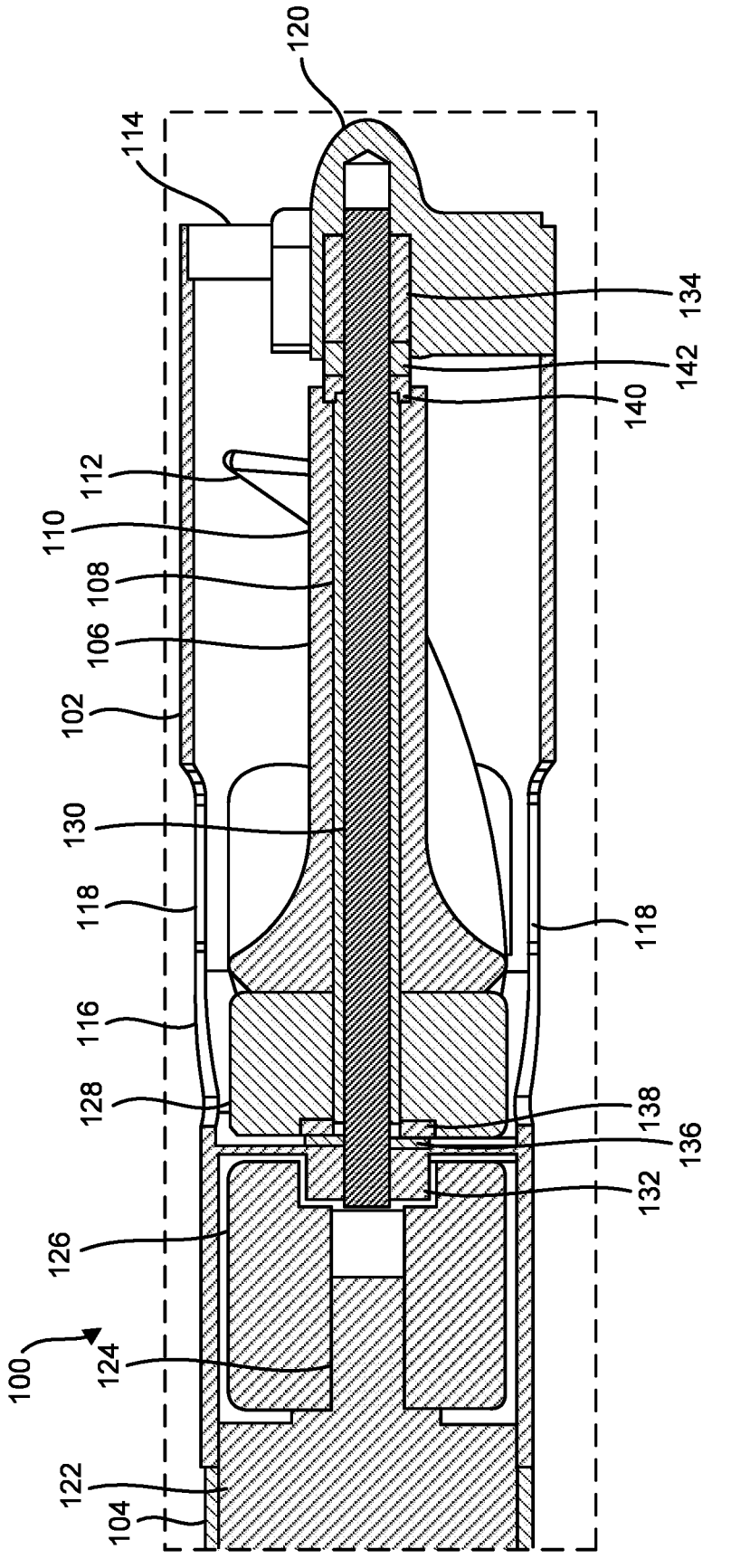
FIG. 2 is an enlarged side sectional view of the blood pump within line 2-2 of FIG. 1, in accordance with embodiments of the subject matter disclosed herein.

With continued reference to FIG. 1 and additional reference to FIG. 2, the blood pump 100 generally includes an impeller housing 102 and a motor housing 104. The impeller housing 102 and/or the motor housing 104 may be constructed of various materials, such as stainless steel or nitinol. In some embodiments, the impeller housing 102 and the motor housing 104 may be integrally or monolithically constructed. In other embodiments, the impeller housing 102 and the motor housing 104 may be separate components configured to be removably or permanently coupled. In some embodiments, the blood pump 100 may lack a separate motor housing 104 and the impeller housing 102 may be coupled directly to the motor 122 described below, or the motor housing 104 may be integrally constructed with the motor 122 described below.

The impeller housing 102 carries an impeller assembly 106 therein. The impeller assembly 106 generally includes an inner tube 108 (for example, a hypotube constructed of stainless steel) and an impeller 110 having one or more impeller blades 112. The inner tube 108 and the impeller 110 rotate together relative to the impeller housing 102 to drive blood through the blood pump 100. More specifically, the impeller 110 causes blood to flow from a blood inlet 114 formed on the impeller housing 102, through the impeller housing 102, and out of a blood outlet 116 formed on the impeller housing 102. As shown in FIGS. 1 and 2, the inlet 114 and/or the outlet 116 may each include multiple apertures. As shown, apertures of the outlet 116 may be formed between adjacent struts 118 of a plurality of struts 118 of the impeller housing 102. In other embodiments, the inlet 114 and/or the outlet 116 may each include a single aperture. As shown in FIGS. 1 and 2, the inlet 114 may be formed on an end portion of the impeller housing 102 and adjacent to a distal support 120 coupled to the impeller housing 102. As shown in FIGS. 1 and 2 the outlet 116 may be formed on a side portion of the impeller housing 102. In other embodiments, the inlet 114 and/or the outlet 116 may be formed on other portions of the impeller housing 102. In some embodiments, the impeller housing 102 may couple to a distally extending cannula (not shown), and the cannula may receive and deliver blood to the inlet 114.

With continued reference to FIGS. 1 and 2, the motor housing 104 carries a motor 122, and the motor 122 is configured to rotatably drive the impeller 110 relative to the impeller housing 102. In the illustrated embodiment, the motor 122 rotates a drive shaft 124, which is coupled to a drive magnet 126 (for example, a samarium cobalt magnet). Rotation of the drive magnet 126 causes rotation of a driven magnet 128 (for example, a samarium cobalt magnet), which is connected to the impeller assembly 106. More specifically, the impeller 110 rotates with the driven magnet 128. In other embodiments, the motor 122 may couple to the impeller assembly 106 via other components.

In some embodiments, a controller (not shown) may be operably coupled to the motor 122 and configured to control the motor 122. In some embodiments, the controller may be disposed within the motor housing 104. In other embodiments, the controller may be disposed outside of the motor housing 104 (for example, in a catheter handle, an independent housing, etc.). In some embodiments, the controller may include multiple components, one or more of which may be disposed within the motor housing 104. In some embodiments, the controller may be, may include, or may be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more central processing units (CPUs), software, hardware, firmware, or any combination of these and/or other components. Although the controller is referred to herein in the singular, the controller may be implemented in multiple instances, distributed across multiple computing devices, instantiated within multiple virtual machines, and/or the like. In other embodiments, the motor 122 may be controlled in other manners.

With further reference to FIGS. 1 and 2, the blood pump 100 includes various components and features that provide reduced device-induced hemolysis compared to conventional devices. More specifically, the blood pump 100 includes a bearing shaft 130, (also referred to herein, interchangeably, simply as a "shaft"—for example a pin or rod constructed of stainless steel, a ceramic, or the like) that is rotatably fixed relative to the impeller housing 102. More specifically, the shaft 130 is fixedly coupled to a proximal hub 132 of the impeller housing 102 and an inner sleeve 134 of the distal support 120 (for example, a silicon sleeve). The bearing shaft 130 rotatably supports the impeller assembly 106 and reduces or eliminates impeller vibrations and other undesirable impeller rotational dynamics, which can cause relatively high shear and hemolysis in conventional blood pumps.

The bearing shaft 130 facilitates use of relatively simple proximal and distal bearings for rotatably coupling the impeller assembly 106 to the impeller housing 102 and the distal support 120 because such bearings do not need to radially capture the impeller assembly 106. More specifically, the blood pump 100 may include one or more proximal thrust bearings and one or more distal thrust bearings. In some embodiments and as illustrated, the blood pump 100 includes a first proximal thrust bearing 136 that abuttingly engages the proximal hub 132 of the impeller housing 102 and a second proximal thrust bearing 138 that abuttingly engages the first proximal thrust bearing 136, the driven magnet 128, and the inner tube 108. In some embodiments and as illustrated, the blood pump 100 includes a first distal thrust bearing 140 that abuttingly engages the impeller 110 and the inner tube 108 and a second distal thrust bearing 142 that abuttingly engages the first distal thrust bearing 140 and the distal support 120, more specifically the inner sleeve 134 of the distal support 120.

The thrust bearings 136, 138, 140, and 142 may take various specific forms and may be constructed of various materials. For example, the first proximal thrust bearing 136, the second proximal thrust bearing 138, the first distal thrust bearing 140, and/or the second distal thrust bearing 142 may be flat bearings. As another example, the first proximal thrust bearing 136 and the second proximal thrust bearing 138 may be constructed of a relatively hard material (that is, the bearings 136 and 138 may have a "hard-on-hard" arrangement). As another example, one of the first proximal thrust bearing 136 and the second proximal thrust bearing 138 may be constructed of a relatively hard material and the other may be constructed of a relatively soft material (that is, the bearings 136 and 138 may have a "hard-on-soft" arrangement). As another example, the first distal thrust bearing 140 and the second distal thrust bearing 142 may be constructed of a relatively hard material. As another example, one of the first distal thrust bearing 140 and the second distal thrust bearing 142 may be constructed of a relatively hard material and the other may be constructed of a relatively soft material. As another example, the first proximal thrust bearing 136, the second proximal thrust bearing 138, the first distal thrust bearing 140, and/or the second distal thrust bearing 142 may be constructed of one or more ceramics, such as silicon nitride, or one or more jewel materials, such as sapphire.

The bearings 136, 138, 140, and 142 may provide one or more advantages over those of conventional blood pumps. For example, the proximal bearings 136 and 138 could reduce or eliminate gaps at the proximal side of the driven magnet 128, and the distal bearings 140 and 142 could reduce or eliminate gaps at the distal side of the impeller assembly 106. As a result, the bearings 136, 138, 140, and 142 could reduce or eliminate potential thrombus formation at those locations, which could lead to premature pump failure. As another example, the bearings 136, 138, 140, and 142 have relatively large contact areas, which mitigates wear. As another example, the proximal bearing 136 and 138 may be relatively thin in an axial direction and thereby facilitate providing a relatively short distance between the drive magnet 126 and the driven magnet 128, which in turn provides relatively high torque transmission to the impeller assembly 106. As yet another example, and in contrast to conventional blood pumps, a compressive load would not need to be applied to the impeller assembly 106 to ensure the bearings 136, 138, 140, and 142 remain seated during pump operation because radial capture of the impeller assembly 106 is provided by the bearing shaft 130. This lack of a compressive load reduces friction and wear.

In some embodiments, the blood pump 100 also includes further advantages compared to conventional blood pumps. For example, the bearing shaft 130 is reinforced along its entire length by the impeller 110, the bearings 136, 138, 140, and 142, the driven magnet 128, the distal support 120, and the impeller housing 102. These components reduce stress on the bearing shaft 130 and increase the overall strength of the blood pump 100.

In some embodiments, the inner sleeve 134 acts as a compression spring and applies a thrust force to the bearings 136, 138, 140, and 142. In these embodiments, the second distal thrust bearing 142 may be axially slidable within the distal support 120. In other embodiments, the blood pump 100 lacks the inner sleeve 134.

Figure 3:
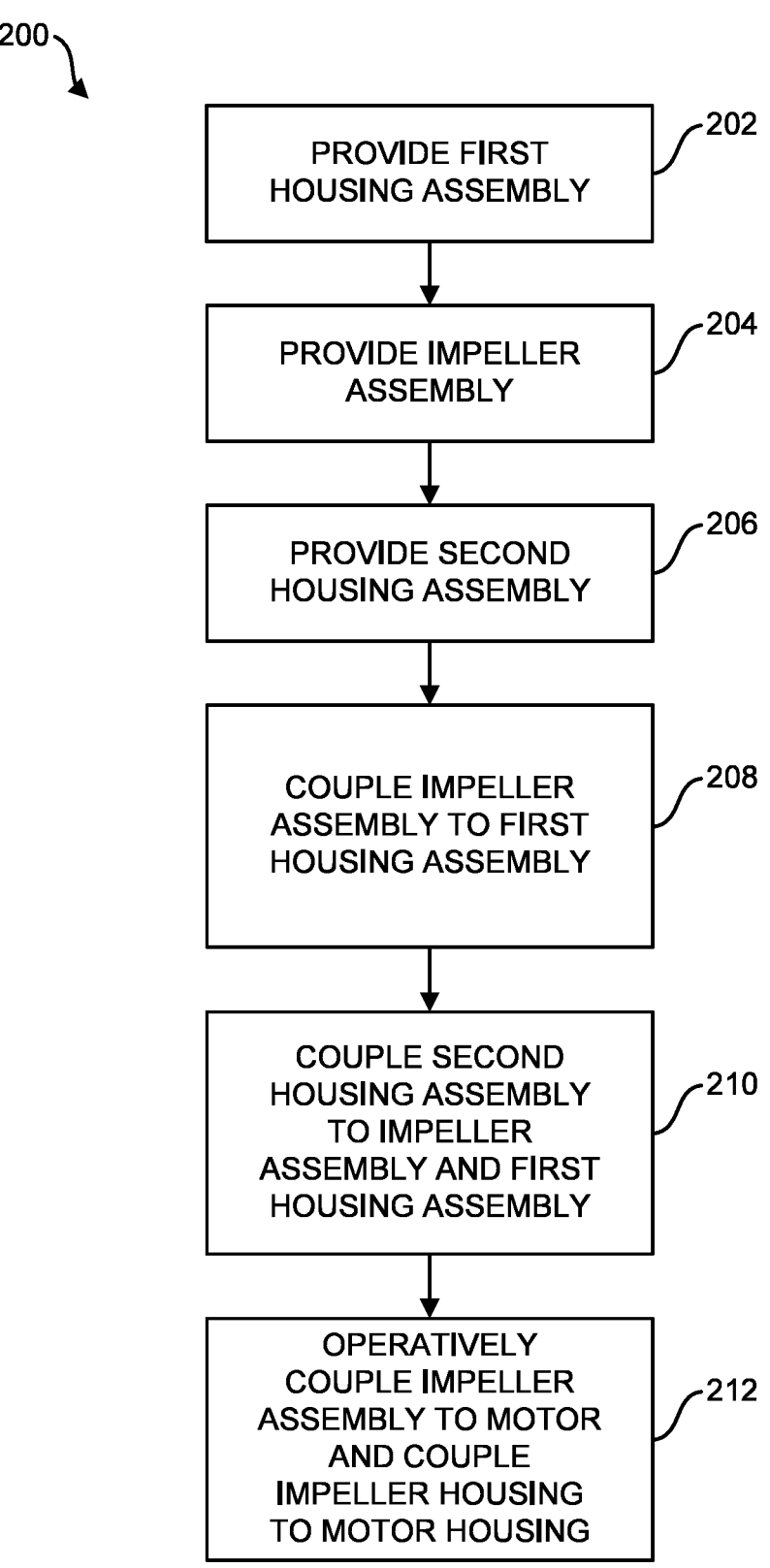
FIG. 3 is a flow diagram of an illustrative method of manufacturing a blood pump, in accordance with embodiments of the subject matter disclosed herein.
Figure 4:
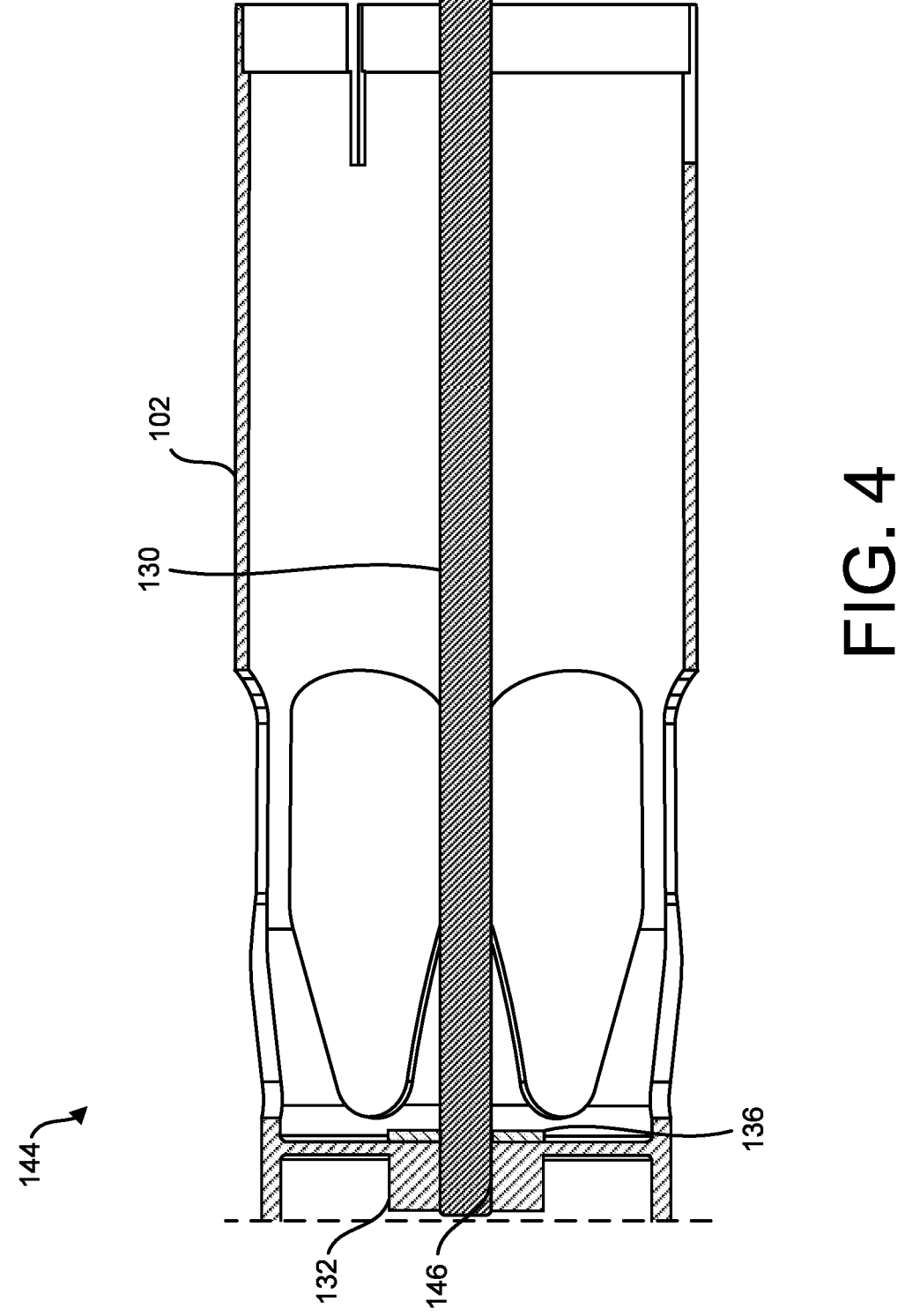
FIG. 4 is a side sectional view of a first housing assembly provided according to the method of FIG. 3, in accordance with embodiments of the subject matter disclosed herein.
Figure 5:
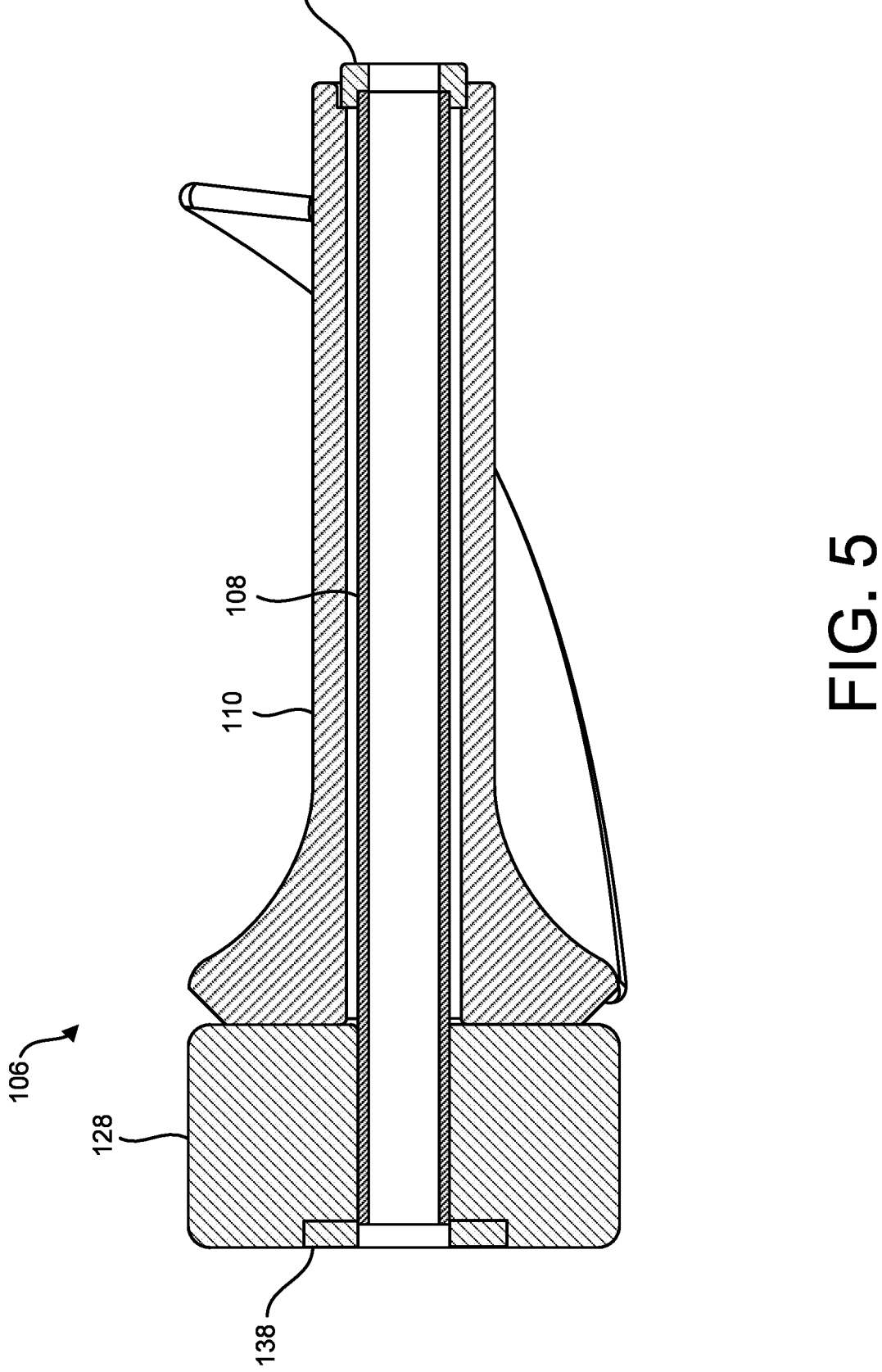
FIG. 5 is a side sectional view of an impeller assembly provided according to the method of FIG. 3, in accordance with embodiments of the subject matter disclosed herein.
Figure 6:
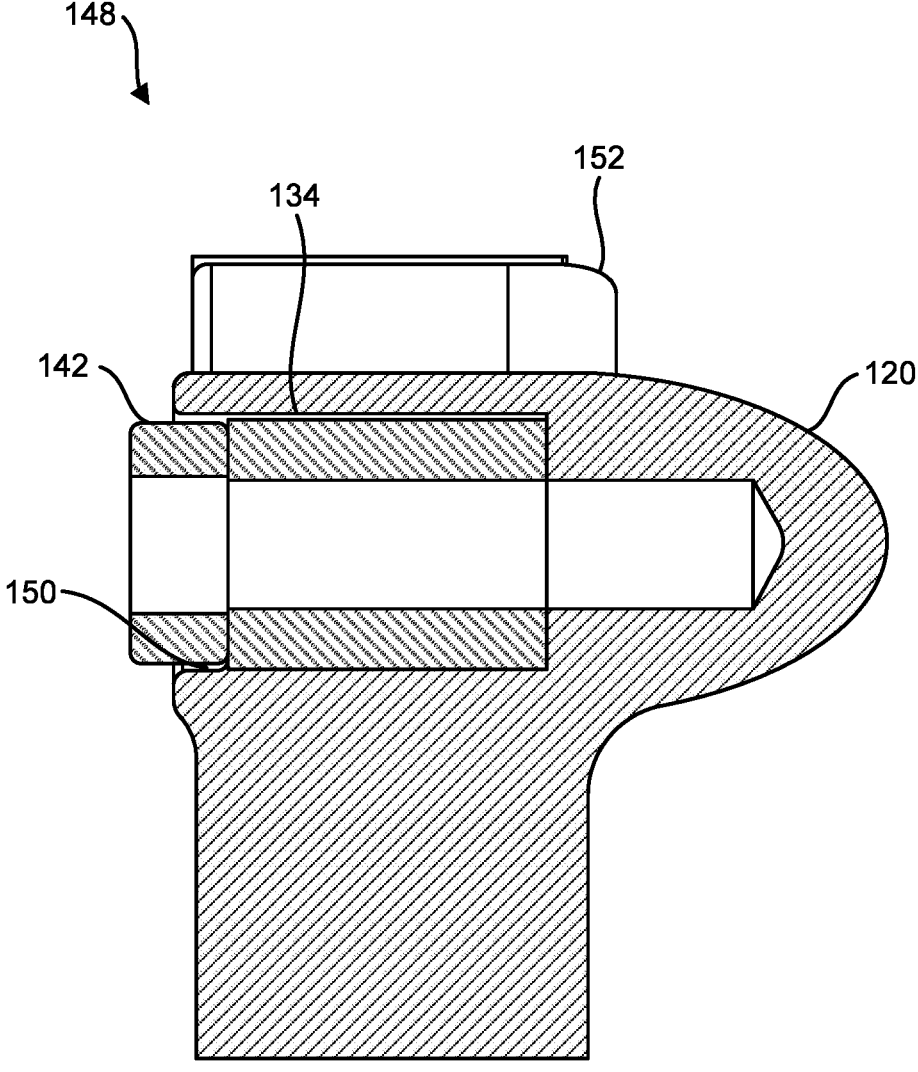
FIG. 6 is a side sectional view of a second housing assembly provided according to the method of FIG. 3, in accordance with embodiments of the subject matter disclosed herein.

FIG. 3 illustrates a flow diagram of an exemplary method 200 of manufacturing a blood pump, in accordance with embodiments of the subject matter disclosed herein, and FIGS. 4-6 illustrate intermediate assemblies associated with the method 200. The method 200 describes features of the blood pump 100, although it is understood that any of the blood pumps contemplated herein could be used in a similar manner. At step 202 and as also shown in FIG. 4, the method begins by providing a first housing assembly 144. More specifically, providing the first housing assembly 144 includes coupling the bearing shaft 130 to the impeller housing 102 such that the shaft 130 is rotatably fixed relative to the impeller housing 102. As illustrated, the shaft 130 may be received in a through opening 146 of the proximal hub 132 of the impeller housing 102. In some embodiments, the bearing shaft 130 is welded or adhesively bonded within the proximal hub 132 of the impeller housing 102. As also shown in FIG. 4, providing the first housing assembly 144 also includes sliding the first proximal thrust bearing 136 over the bearing shaft 130 and abutting the proximal hub 132 of the impeller housing 102. In some embodiments, the first proximal thrust bearing 136 is adhesively bonded to the proximal hub 132 of the impeller housing 102. Next or simultaneously and at step 204 and as shown in FIG. 5, the method includes providing the impeller assembly 106. More specifically, providing the impeller assembly 106 includes coupling the impeller 110, the driven magnet 128, the second proximal thrust bearing 138, and the first distal thrust bearing 140 to the inner tube 108 such that these components are rotatably fixed relative to each other. In some embodiments, the impeller 110 is overmolded onto the inner tube 108. In some embodiments, the driven magnet 128 is slid over the proximal end of the inner tube 108 and adhesively bonded to the proximal end of the impeller 110. In some embodiments, the second proximal thrust bearing 138 is slid over the inner tube 108 and adhesively bonded to the proximal end of the driven magnet 128. In some embodiments, the first distal thrust bearing 140 is slid over the distal end of the inner tube 108 and adhesively bonded to the distal end of the impeller 110. Next or simultaneously and at step 206 and as shown in FIG. 6, the method includes providing a second housing assembly 148. More specifically, providing the second housing assembly 148 includes coupling the sleeve 134 and the second distal thrust bearing 142 to the distal support 120 such that these components are rotatably fixed relative to each other. In some embodiments, the sleeve 134 is inserted in a blind opening 150 of the distal support 120, and the second distal thrust bearing 142 abuts the proximal end of the sleeve 134 and is adhesively bonded to the distal support 120.

With continued reference to FIG. 3 and further general reference to FIGS. 4-6, the method continues at step 208 by coupling the impeller assembly 106 (FIG. 5) to the first housing assembly 144 (FIG. 4). More specifically, coupling the impeller assembly 106 to the first housing assembly 144 includes sliding the inner tube 108 along the bearing shaft 130 such that the second proximal thrust bearing 138 loosely abuts the first proximal thrust bearing 136 (that is, without applying a load between the bearings) and the impeller assembly 106 is rotatable relative to the first housing assembly 144. In some embodiments, coupling the impeller assembly 106 to the first housing assembly 144 additionally includes providing a lubricant between the inner tube 108 and the bearing shaft 130. Next, the method continues at step 210 by coupling the second housing assembly 148 (FIG. 6) to the impeller assembly 106 and the first housing assembly 144. More specifically, coupling the second housing assembly 148 to the impeller assembly 106 and the first housing assembly 144 includes inserting the bearing shaft 130 into the sleeve 134 and the distal support 120 such that the first distal thrust bearing 140 loosely abuts the second distal thrust bearing 142 (that is, without applying a load between the bearings). In some embodiments, coupling the second housing assembly 148 to the impeller assembly 106 and the first housing assembly 144 includes welding or adhesively bonding the sleeve 134 of the distal support 120 to the bearing shaft 130. In some embodiments, coupling the second housing assembly 148 to the impeller assembly 106 and the first housing assembly 144 includes welding or adhesively bonding one or more radially extending arms 152 of the distal support 120 to the impeller housing 102. The method concludes at step 212 by operatively coupling the impeller assembly 106 to the motor 122 (FIGS. 1 and 2) and coupling the impeller housing 102 to the motor housing 104 (FIGS. 1 and 2). In some embodiments, operatively coupling the impeller assembly 106 to the motor 122 includes magnetically coupling the driven magnet 128 to the drive magnet 126 (FIGS. 1 and 2). In some embodiments, coupling the impeller housing 102 to the motor housing 104 includes welding or adhesively bonding the impeller housing 102 to the motor housing 104.

Figure 7:
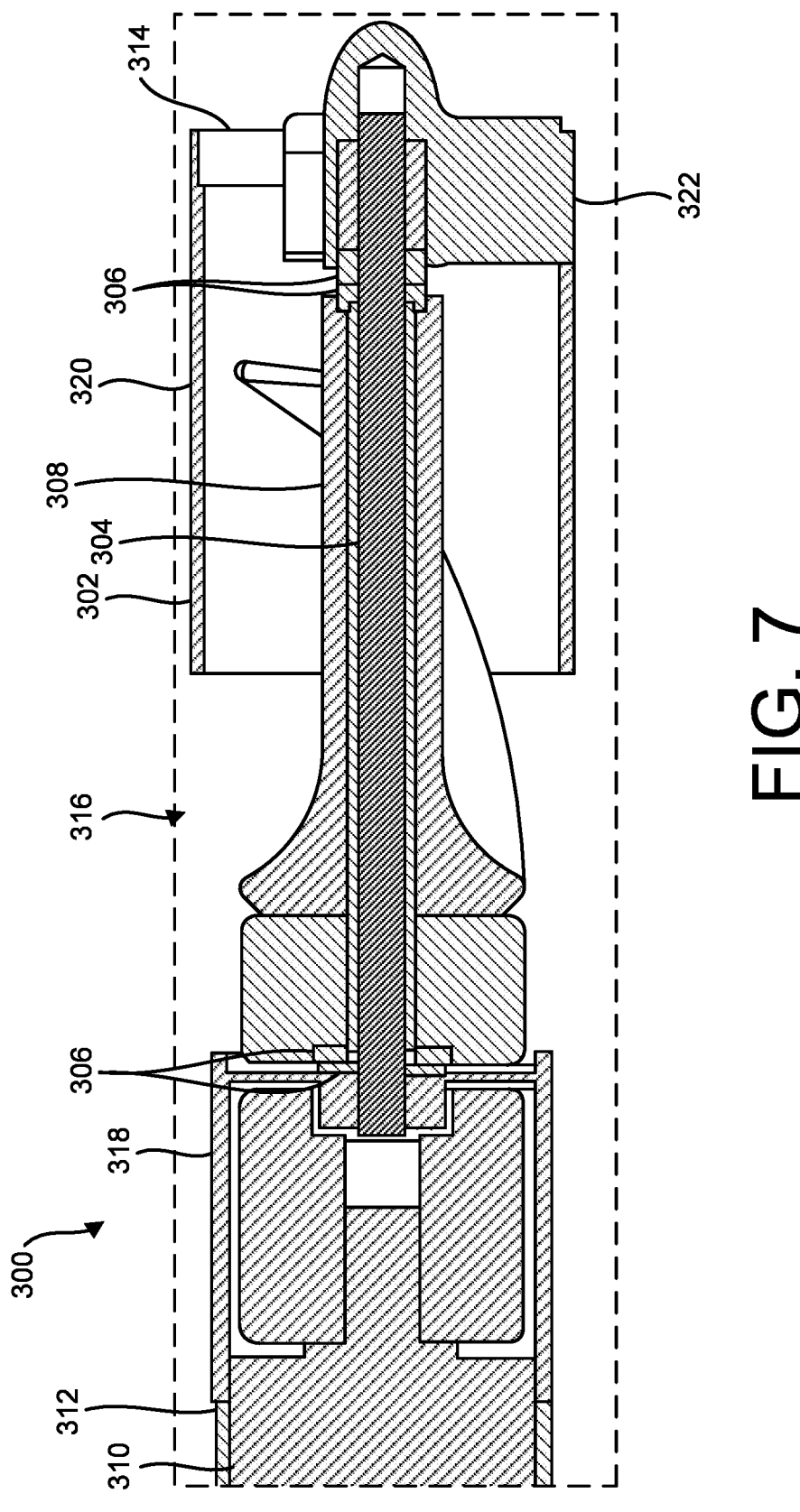
FIG. 7 is a side sectional view of another illustrative blood pump, in accordance with embodiments of the subject matter disclosed herein.

FIG. 7 depicts a partial side sectional view of another illustrative mechanical circulatory support device or blood pump 300 in accordance with embodiments of the subject matter disclosed herein. The blood pump 300 is generally similar to the blood pump 100 described above. That is, the blood pump 300 includes an impeller housing 302 that fixedly couples to a bearing shaft 304. The bearing shaft 304 rotatably supports, via thrust bearings 306, an impeller assembly 308. The impeller assembly 308 is rotatably driven by a motor 310, and the motor 310 is carried in a motor housing 312 coupled to the impeller housing 302. The impeller housing 302 also includes an inlet 314 and an outlet 316 that facilitate blood flow through the blood pump 300. Unlike the blood pump 100 described above, however, the impeller housing 302 includes a proximal impeller housing portion 318 and a distal impeller housing portion 320 that are completely disposed apart and thereby form the outlet 316 therebetween. Stated another way, the proximal impeller housing portion 318 and the distal impeller housing portion 320 are only indirectly coupled via the bearing shaft 304, and the proximal impeller housing portion 318 and the distal impeller housing portion 320 thereby form the outlet 316 therebetween. Stated yet another way, the impeller housing 302 lacks struts (see, for comparison and for example, the struts 118 of the blood pump 100) coupling the proximal impeller housing portion 318 and the distal impeller housing portion 320. As a result, shear induced by struts is eliminated, which results in reduced hemolysis.

Figure 8:
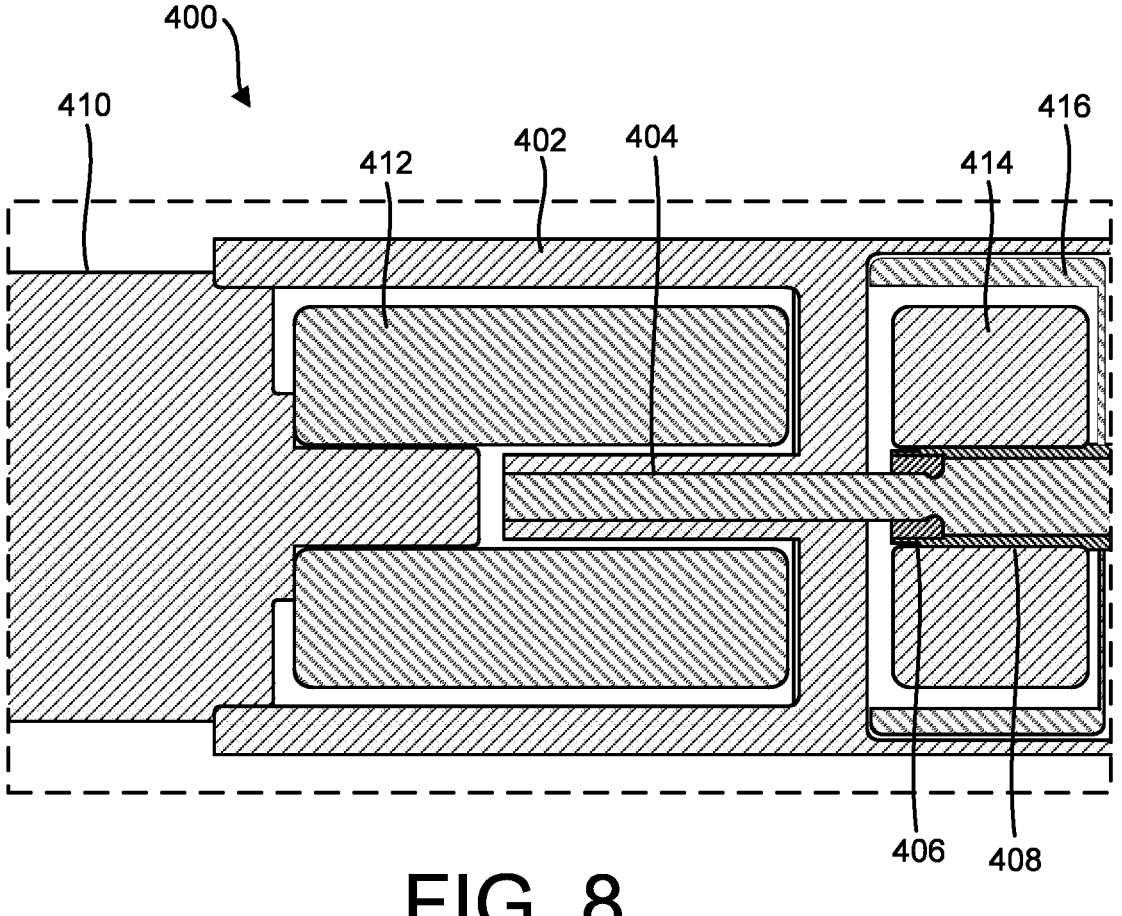
FIG. 8 is a side sectional view of yet another illustrative blood pump, in accordance with embodiments of the subject matter disclosed herein.

FIG. 8 depicts a partial side sectional view of another illustrative mechanical circulatory support device or blood pump 400 in accordance with embodiments of the subject matter disclosed herein. The blood pump 400 is generally similar to the blood pump 100 described above. That is, the blood pump 400 includes an impeller housing 402 that fixedly couples to a bearing shaft 404. The bearing shaft 404 rotatably supports, via bearings (one bearing 406 being visible), an impeller assembly (an inner tube 408 of the impeller assembly being visible). The impeller assembly is rotatably driven by a motor 410 via a drive magnet 412 and a driven magnet 414, and the motor 410 is coupled to the impeller housing 402. Additionally, and unlike the blood pump 100 described above, the impeller housing 402 also carries a protector 416, which may also be referred to as a proximal seal. As illustrated, the protector 416 may be positioned both radially outwardly and distally relative to the driven magnet 414. As such, the protector 416 may inhibit blood from contacting the driven magnet 414 and thereby inhibit corrosion and/or other wear. In some embodiments, the protector 416 may be configured to maintain a volume of protective fluid in contact with the driven magnet 414. The protective fluid may be, for example, a hydrophobic lubricant. The protective fluid may be any type of hydrophobic lubricant suitable for use in a blood pump. For example, the protective fluid may be a modified silicone lubricant such as a modified Polydimethylsiloxane (PDMS). In other embodiments, the protective fluid may be an oil-based lubricant, a synthetic oil, a carbon-based lubricant, and/or the like. In some embodiments, the protector 416 may rotate with the impeller assembly and the driven magnet 414 relative to the impeller housing 402. In some embodiments, the protector 416 may be fixed relative to the impeller housing 402.

Generally, the blood pump 300 may be manufactured according to the method 200 except that providing the second housing assembly (step 206) may include coupling the distal support 322 to the distal impeller housing portion 320, for example, via welding or adhesive bonding. The second housing assembly may be subsequently coupled to the first housing assembly and the impeller assembly.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A percutaneous circulatory support device, comprising:
a motor configured to rotate a drive shaft which is coupled to a drive magnet;
an impeller;
a driven magnet configured to rotate with the impeller, wherein rotation of the drive magnet causes rotation of the driven magnet;
an impeller housing comprising an inlet and an outlet; and
a shaft rotatably fixed relative to the impeller housing;
wherein the outlet is formed of a side portion of the impeller housing; and
wherein the motor is operable to rotatably drive the impeller relative to the shaft and the impeller housing to cause blood to flow into the inlet, through the impeller housing, and out of the outlet.

2. The percutaneous circulatory support device of claim 1, further comprising a thrust bearing coupling the impeller to the impeller housing.

3. The percutaneous circulatory support device of claim 2, wherein the thrust bearing is a proximal thrust bearing, and further comprising a distal thrust bearing coupling the impeller to the impeller housing.

4. The percutaneous circulatory support device of claim 1, further comprising an impeller assembly, the impeller assembly comprising the impeller and an inner tube rotatably supported by the shaft, and the impeller is rotatably fixed relative to the inner tube.

5. The percutaneous circulatory support device of claim 4, wherein the inner tube and the impeller are rotatably fixed relative to the driven magnet;
wherein the motor is operable to rotatably drive the impeller, via the drive magnet and the driven magnet, and thereby cause blood to flow into the inlet, through the impeller housing, and out of the outlet.

6. The percutaneous circulatory support device of claim 1, wherein the impeller housing comprises a proximal impeller housing portion and a distal impeller housing portion, the proximal impeller housing portion and the distal impeller housing portion being completely disposed apart and thereby forming the outlet therebetween.

7. The percutaneous circulatory support device of claim 6, wherein the distal impeller housing portion comprises the inlet.

8. The percutaneous circulatory support device of claim 1, wherein the impeller housing comprises a proximal impeller housing portion and a distal impeller housing portion, the proximal impeller housing portion and the distal impeller housing portion only being indirectly coupled via the shaft, and the proximal impeller housing and the distal impeller housing thereby forming the outlet therebetween.

9. The percutaneous circulatory support device of claim 8, wherein the distal impeller housing portion comprises the inlet.

10. A percutaneous circulatory support device, comprising:

a motor configured to rotate a drive shaft;

a drive magnet fixed to the drive shaft;

an impeller;

a driven magnet configured to rotate with the impeller, wherein rotation of the drive magnet causes rotation of the driven magnet;

an impeller housing comprising an inlet and an outlet, the impeller disposed within the impeller housing;

a distal support coupled to the impeller housing opposite the motor; and a shaft rotatably fixed relative to the impeller housing and the distal support;

wherein the outlet is formed on a side portion of the impeller housing; and wherein the motor is operable to rotatably drive the impeller relative to the shaft and impeller housing and thereby cause blood to flow into the inlet, through the impeller housing, and out of the outlet.

11. The percutaneous circulatory support device of claim 10, further comprising a thrust bearing coupled to the impeller.

12. The percutaneous circulatory support device of claim 11, wherein the thrust bearing is a proximal thrust bearing, and further comprising a distal thrust bearing coupled to the impeller.

13. The percutaneous circulatory support device of claim 10, further comprising an impeller assembly, the impeller assembly comprising the impeller and an inner tube rotatably supported by the shaft, and the impeller is rotatably fixed relative to the inner tube.

14. The percutaneous circulatory support device of claim 13, further comprising:

a drive magnet operably coupled to the motor; and a driven magnet operably coupled to the drive magnet, the inner tube and the impeller being rotatably fixed relative to the driven magnet;

wherein the motor is operable to rotatably drive the impeller, via the drive magnet and the driven magnet, and thereby cause blood to flow into the inlet, through the impeller housing, and out of the outlet.

15. A method of manufacturing a percutaneous circulatory support device, the method comprising:

coupling a shaft to an impeller housing such that the shaft is rotatably fixed relative to the impeller housing, wherein the impeller housing comprises an outlet formed on a side portion of the impeller housing;

coupling an impeller to the shaft such that the impeller is disposed within the impeller housing and rotatably supported by the shaft; and operatively coupling the impeller to a motor, the motor configured to rotate a drive shaft which is coupled to a drive magnet, wherein rotation of the drive magnet causes rotation of a driven magnet coupled to the impeller to rotate the impeller, and wherein the motor is operable to rotatably drive the impeller relative to the shaft and the impeller housing to cause blood to flow into an inlet of the impeller housing, through the impeller housing, and out of the outlet.

16. The method of claim 15, further comprising coupling a thrust bearing to the shaft and the impeller housing before coupling the impeller to the shaft.

17. The method of claim 15, further comprising coupling an inner tube to the impeller such that the impeller is rotatably fixed relative to the inner tube, and wherein coupling the impeller to the shaft comprises together coupling the inner tube and the impeller to the shaft.

18. The method of claim 15, further comprising coupling a proximal thrust bearing and a distal thrust bearing to the impeller before coupling the impeller to the shaft.

* * * * *